(12) United States Patent
Rice

(10) Patent No.: US 7,762,907 B2
(45) Date of Patent: *Jul. 27, 2010

(54) METAL WOOD CLUB WITH IMPROVED HITTING FACE

(75) Inventor: Scott A. Rice, San Diego, CA (US)

(73) Assignee: Acushnet Company, Fairhaven, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/487,676

(22) Filed: Jun. 19, 2009

(65) Prior Publication Data

US 2009/0258724 A1 Oct. 15, 2009

Related U.S. Application Data

(63) Continuation of application No. 11/499,323, filed on Aug. 4, 2006, now Pat. No. 7,549,934, which is a continuation-in-part of application No. 11/221,221, filed on Sep. 7, 2005.

(51) Int. Cl.
*A63B 53/04* (2006.01)
(52) U.S. Cl. ........................ 473/329; 473/345; 473/346; 473/349
(58) Field of Classification Search ......... 473/324–350, 473/287–292
See application file for complete search history.

(56) References Cited

U.S. PATENT DOCUMENTS

| | | | |
|---|---|---|---|
| 1,318,325 A | 10/1919 | Klin | |
| 1,319,233 A | 10/1919 | Mattern | |
| 1,467,435 A | 9/1923 | Kinnear | |
| 1,525,352 A | 2/1925 | Aitken | |
| 1,543,691 A | 6/1925 | Beat | |
| 1,582,836 A | 4/1926 | Link | |
| 1,589,363 A | 6/1926 | Butchart | |
| 1,595,589 A | 8/1926 | Tyler | |
| 1,605,551 A | 11/1926 | Mattern | |
| 1,699,874 A | 1/1929 | Buhrke | |
| 1,704,119 A | 3/1929 | Buhrke | |
| 1,704,165 A | 3/1929 | Buhrke | |
| 1,720,867 A | 7/1929 | Webster et al. | |
| 2,034,936 A | 3/1936 | Barnhart | |
| 2,087,685 A | 7/1937 | Hackney | |
| 3,567,228 A | 3/1971 | Lynn | |

(Continued)

FOREIGN PATENT DOCUMENTS

CN 1114911 1/1996

(Continued)

OTHER PUBLICATIONS

Golf Digest, Sep. 1982, p. 25.

(Continued)

*Primary Examiner*—Sebastiano Passaniti
(74) *Attorney, Agent, or Firm*—Randy K. Chang

(57) ABSTRACT

A hitting face of a golf club head having a location of longest characteristic time shifted away from the geometric center of the hitting face. The hitting face of the club head has varying thickness, with a thickest portion being at or near the geometric center of the plate-like hitting face. A second thickened portion of the hitting face substantially surrounds the thickest portion. The portions of varying thickness taper therebetween for relatively smooth cross-sectional profiles.

23 Claims, 3 Drawing Sheets

U.S. PATENT DOCUMENTS

| | | |
|---|---|---|
| 3,571,900 A | 3/1971 | Hardesty |
| 3,625,518 A | 12/1971 | Solheim |
| 3,659,855 A | 5/1972 | Hardesty |
| 3,863,932 A | 2/1975 | Lezatte |
| 3,985,363 A | 10/1976 | Jepson et al. |
| 4,023,802 A | 5/1977 | Jepson et al. |
| 4,193,601 A | 3/1980 | Reid, Jr. et al. |
| 4,213,613 A | 7/1980 | Nygren |
| 4,214,754 A | 7/1980 | Zebelean |
| D267,965 S | 2/1983 | Kobayashi |
| 4,429,879 A | 2/1984 | Schmidt |
| 4,432,549 A | 2/1984 | Zebelean |
| 4,449,707 A | 5/1984 | Hayashi et al. |
| 4,451,041 A | 5/1984 | Hayashi et al. |
| 4,451,042 A | 5/1984 | Hayashi et al. |
| 4,465,221 A | 8/1984 | Schmidt |
| 4,471,961 A | 9/1984 | Masghati et al. |
| 4,489,945 A | 12/1984 | Kobayashi |
| 4,511,145 A | 4/1985 | Schmidt |
| 4,762,324 A | 8/1988 | Anderson |
| 4,792,140 A | 12/1988 | Yamaguchi et al. |
| 4,826,172 A | 5/1989 | Antonious |
| 4,842,243 A | 6/1989 | Butler |
| 4,913,438 A | 4/1990 | Anderson |
| 4,915,385 A | 4/1990 | Anderson |
| 4,915,386 A | 4/1990 | Antonious |
| 4,919,430 A | 4/1990 | Antonious |
| 4,919,431 A | 4/1990 | Antonious |
| 4,921,252 A | 5/1990 | Antonious |
| 4,928,965 A | 5/1990 | Yamaguchi et al. |
| 4,930,781 A | 6/1990 | Allen |
| 4,932,658 A | 6/1990 | Antonious |
| 4,955,610 A | 9/1990 | Creighton et al. |
| D312,858 S | 12/1990 | Anderson et al. |
| 5,000,454 A | 3/1991 | Soda |
| 5,014,993 A * | 5/1991 | Antonious .................. 473/350 |
| 5,024,437 A | 6/1991 | Anderson |
| 5,028,049 A | 7/1991 | McKeighen |
| 5,046,733 A | 9/1991 | Antonious |
| 5,056,705 A | 10/1991 | Wakita et al. |
| 5,060,951 A | 10/1991 | Allen |
| 5,067,715 A | 11/1991 | Schmidt et al. |
| 5,090,702 A | 2/1992 | Viste |
| 5,094,383 A | 3/1992 | Anderson et al. |
| 5,106,094 A | 4/1992 | Desbiolles et al. |
| 5,141,230 A | 8/1992 | Antonious |
| 5,163,682 A | 11/1992 | Schmidt et al. |
| 5,180,166 A | 1/1993 | Schmidt et al. |
| 5,183,255 A | 2/1993 | Antonious |
| 5,213,328 A | 5/1993 | Long et al. |
| 5,221,087 A | 6/1993 | Fenton et al. |
| 5,240,252 A | 8/1993 | Schmidt et al. |
| 5,242,167 A | 9/1993 | Antonious |
| 5,255,918 A | 10/1993 | Anderson et al. |
| 5,261,663 A | 11/1993 | Anderson |
| 5,261,664 A | 11/1993 | Anderson |
| 5,271,621 A | 12/1993 | Lo |
| 5,292,129 A | 3/1994 | Long et al. |
| 5,295,689 A | 3/1994 | Lundberg |
| 5,301,945 A | 4/1994 | Schmidt et al. |
| 5,318,300 A | 6/1994 | Schmidt et al. |
| 5,328,184 A | 7/1994 | Antonious |
| 5,344,140 A | 9/1994 | Anderson |
| 5,346,218 A | 9/1994 | Wyte |
| 5,351,958 A | 10/1994 | Helmstetter |
| 5,358,249 A | 10/1994 | Mendralla |
| 5,362,047 A | 11/1994 | Shaw et al. |
| 5,362,055 A | 11/1994 | Rennie |
| 5,366,223 A | 11/1994 | Werner et al. |
| 5,380,010 A | 1/1995 | Werner et al. |
| 5,390,924 A | 2/1995 | Antonious |
| 5,395,113 A | 3/1995 | Antonious |
| 5,397,126 A | 3/1995 | Allen |
| 5,401,021 A | 3/1995 | Allen |
| 5,405,136 A | 4/1995 | Hardman |
| 5,405,137 A | 4/1995 | Vincent et al. |
| 5,407,202 A | 4/1995 | Igarashi |
| RE34,925 E | 5/1995 | McKeighen |
| 5,417,419 A | 5/1995 | Anderson et al. |
| 5,417,559 A | 5/1995 | Schmidt |
| 5,423,535 A | 6/1995 | Shaw et al. |
| 5,429,357 A | 7/1995 | Kobayashi |
| 5,431,396 A | 7/1995 | Shieh |
| 5,433,440 A | 7/1995 | Lin |
| 5,447,307 A | 9/1995 | Antonious |
| 5,447,309 A | 9/1995 | Vincent |
| 5,451,056 A | 9/1995 | Manning |
| 5,460,376 A | 10/1995 | Schmidt et al. |
| 5,467,983 A | 11/1995 | Chen |
| 5,470,069 A | 11/1995 | Schmidt et al. |
| 5,474,296 A | 12/1995 | Schmidt et al. |
| 5,482,279 A | 1/1996 | Antonious |
| 5,497,993 A | 3/1996 | Shan |
| 5,505,453 A | 4/1996 | Mack |
| 5,522,593 A | 6/1996 | Kobayashi et al. |
| 5,524,331 A | 6/1996 | Pond |
| 5,533,729 A | 7/1996 | Leu |
| 5,536,006 A | 7/1996 | Shieh |
| 5,547,630 A | 8/1996 | Schmidt |
| 5,549,297 A | 8/1996 | Mahaffey |
| 5,564,994 A | 10/1996 | Chang |
| 5,584,770 A | 12/1996 | Jensen |
| 5,595,552 A | 1/1997 | Wright et al. |
| 5,611,741 A | 3/1997 | Schmidt et al. |
| 5,611,742 A | 3/1997 | Kobayashi |
| D379,393 S | 5/1997 | Kubica et al. |
| 5,626,530 A | 5/1997 | Schmidt et al. |
| 5,643,104 A | 7/1997 | Antonious |
| 5,643,108 A | 7/1997 | Cheng |
| 5,643,110 A | 7/1997 | Igarashi |
| 5,649,872 A | 7/1997 | Antonious |
| 5,651,409 A | 7/1997 | Sheehan |
| 5,655,976 A | 8/1997 | Rife |
| 5,669,827 A | 9/1997 | Nagamoto |
| 5,669,829 A | 9/1997 | Lin |
| 5,674,132 A | 10/1997 | Fisher |
| D387,113 S | 12/1997 | Burrows |
| 5,695,411 A | 12/1997 | Wright et al. |
| 5,709,614 A | 1/1998 | Horiba |
| 5,709,615 A | 1/1998 | Liang |
| 5,711,722 A | 1/1998 | Miyajima et al. |
| 5,716,292 A | 2/1998 | Huang |
| 5,718,641 A | 2/1998 | Lin |
| 5,720,673 A | 2/1998 | Anderson |
| 5,743,813 A | 4/1998 | Chen et al. |
| 5,753,170 A | 5/1998 | Muang |
| 5,755,624 A | 5/1998 | Helmstetter |
| 5,762,567 A | 6/1998 | Antonious |
| 5,766,092 A | 6/1998 | Mimeur et al. |
| 5,766,094 A | 6/1998 | Mahaffey et al. |
| 5,766,095 A | 6/1998 | Antonious |
| 5,776,011 A | 7/1998 | Su et al. |
| 5,807,190 A | 9/1998 | Krumme et al. |
| 5,827,132 A | 10/1998 | Bamber |
| RE35,955 E | 11/1998 | Lu |
| D401,652 S | 11/1998 | Burrows |
| 5,830,084 A | 11/1998 | Kosmatka |
| 5,839,975 A | 11/1998 | Lundberg |
| 5,842,934 A | 12/1998 | Ezaki et al. |
| 5,851,159 A | 12/1998 | Burrows |
| 5,863,261 A | 1/1999 | Eggiman |
| 5,873,791 A | 2/1999 | Allen |
| 5,873,795 A | 2/1999 | Wozny et al. |
| D406,294 S | 3/1999 | Burrows |

| | | | | | | |
|---|---|---|---|---|---|---|
| 5,888,148 | A | 3/1999 | Allen | JP | 59207169 | 11/1984 |
| 5,890,973 | A | 4/1999 | Gamble | JP | 61033682 | 2/1986 |
| D411,272 | S | 6/1999 | Burrows | JP | 61162967 | 7/1986 |
| 5,908,357 | A | 6/1999 | Hsieh | JP | 61181477 | 8/1986 |
| 5,921,872 | A | 7/1999 | Kobayashi | JP | 61185281 | 8/1986 |
| 5,931,746 | A | 8/1999 | Soong | JP | 61240977 | 10/1986 |
| 5,935,019 | A | 8/1999 | Yamamoto | JP | 1244770 | 9/1989 |
| 5,938,541 | A | 8/1999 | Allen et al. | JP | 02130519 | 5/1990 |
| 5,941,782 | A | 8/1999 | Cook | JP | 4020357 | 1/1992 |
| 5,944,619 | A | 8/1999 | Cameron | JP | 4327864 | 11/1992 |
| 5,954,596 | A | 9/1999 | Noble et al. | JP | 5212526 | 8/1993 |
| D415,807 | S | 10/1999 | Werner et al. | JP | 05237207 | 9/1993 |
| 5,961,394 | A | 10/1999 | Minabe | JP | 6007487 | 1/1994 |
| 5,967,905 | A | 10/1999 | Nakahara et al. | JP | 06031016 | 2/1994 |
| 5,971,868 | A | 10/1999 | Kosmatka | JP | 6114126 | 4/1994 |
| 5,993,329 | A | 11/1999 | Shieh | JP | 6126002 | 5/1994 |
| 6,007,432 | A | 12/1999 | Kosmatka | JP | 6154367 | 6/1994 |
| 6,027,416 | A | 2/2000 | Schmidt et al. | JP | 6182005 | 7/1994 |
| 6,048,278 | A * | 4/2000 | Meyer et al. ............... 473/345 | JP | 6269518 | 9/1994 |
| 6,139,445 | A | 10/2000 | Werner et al. | JP | 8168541 | 7/1996 |
| 6,143,169 | A | 11/2000 | Lee | JP | 8243194 | 9/1996 |
| 6,152,833 | A | 11/2000 | Werner et al. | JP | 8280853 | 10/1996 |
| 6,248,025 | B1 | 6/2001 | Murphy | JP | 8280854 | 10/1996 |
| 6,319,150 | B1 | 11/2001 | Werner et al. | JP | 8294550 | 11/1996 |
| 6,338,683 | B1 | 1/2002 | Kosmatka | JP | 9028842 | 2/1997 |
| 6,368,234 | B1 | 4/2002 | Galloway | JP | 9047531 | 2/1997 |
| 6,381,828 | B1 | 5/2002 | Boyce | JP | 9154985 | 6/1997 |
| 6,390,933 | B1 | 5/2002 | Galloway et al. | JP | 9168613 | 6/1997 |
| 6,398,666 | B1 | 6/2002 | Evans et al. | JP | 9192270 | 7/1997 |
| 6,435,982 | B1 | 8/2002 | Galloway et al. | JP | 9192273 | 7/1997 |
| 6,475,101 | B2 * | 11/2002 | Burrows .................... 473/334 | JP | 9239074 | 9/1997 |
| 6,508,722 | B1 * | 1/2003 | McCabe et al. ............. 473/330 | JP | 9239075 | 9/1997 |
| 6,605,007 | B1 | 8/2003 | Bissonnette et al. | JP | 9248353 | 9/1997 |
| 6,755,627 | B2 | 6/2004 | Chang | JP | 9294833 | 11/1997 |
| 6,899,638 | B2 | 5/2005 | Iwata et al. | JP | 9299519 | 11/1997 |
| 6,905,061 | B2 * | 6/2005 | Song .......................... 228/115 | JP | 10024126 | 1/1998 |
| 7,029,403 | B2 * | 4/2006 | Rice et al. .................. 473/329 | JP | 10024128 | 1/1998 |
| 7,101,289 | B2 * | 9/2006 | Gibbs et al. ................ 473/329 | JP | 10085369 | 4/1998 |
| 7,147,572 | B2 * | 12/2006 | Kohno ....................... 473/314 | JP | 10118227 | 5/1998 |
| 7,207,898 | B2 * | 4/2007 | Rice et al. .................. 473/329 | JP | 10137372 | 5/1998 |
| 7,220,190 | B2 * | 5/2007 | Hirano ...................... 473/342 | JP | 10155943 | 6/1998 |
| 7,226,366 | B2 | 6/2007 | Galloway et al. | JP | 10258142 | 9/1998 |
| 7,261,643 | B2 * | 8/2007 | Rice et al. .................. 473/329 | JP | 10263121 | 10/1998 |
| 7,331,877 | B2 * | 2/2008 | Yamaguchi et al. ......... 473/329 | JP | 10323410 | 12/1998 |
| 7,361,099 | B2 * | 4/2008 | Rice et al. .................. 473/329 | JP | 10337347 | 12/1998 |
| 7,520,819 | B2 * | 4/2009 | Rice et al. .................. 473/329 | | | |
| 7,549,934 | B2 * | 6/2009 | Rice .......................... 473/329 | | | |

FOREIGN PATENT DOCUMENTS

| | | | |
|---|---|---|---|
| GB | 2268693 | A | 1/1994 |
| GB | 2331938 | A | 6/1999 |

OTHER PUBLICATIONS

Golf Digest, Dec. 1981, p. 58-59.
"Variable Face Thickness Technology," Calloway Golf advertisement, undated.

* cited by examiner

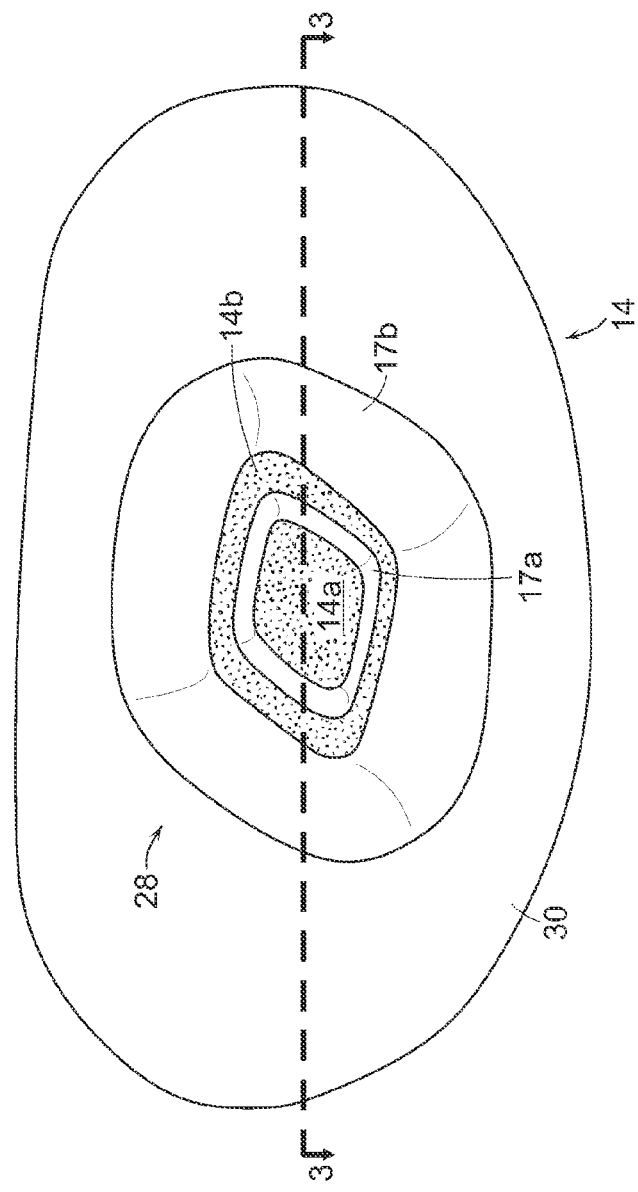
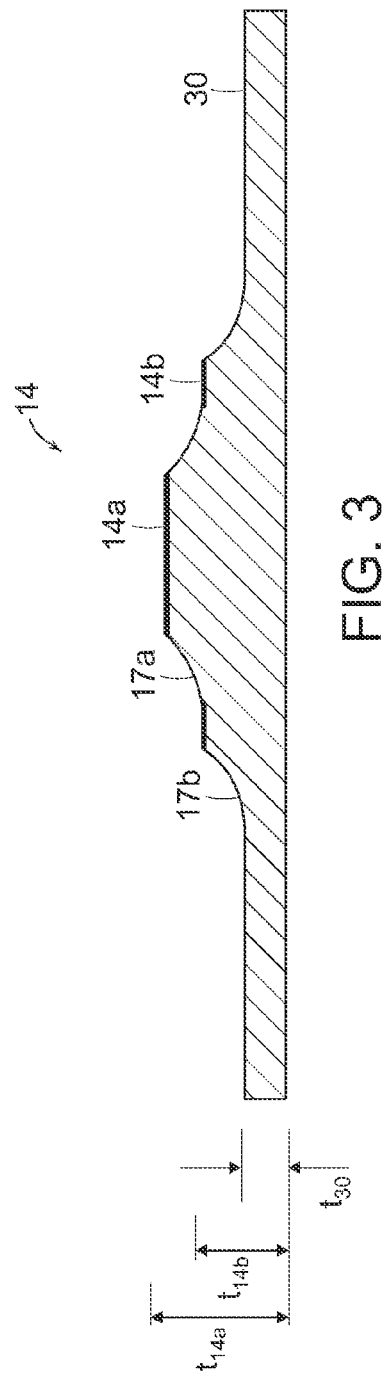
FIG. 2
FIG. 3

METAL WOOD CLUB WITH IMPROVED HITTING FACE

CROSS-REFERENCE TO RELATED APPLICATION

The present application is a continuation of U.S. patent application Ser. No. 11/499,323, filed on Aug. 4, 2006, now U.S. Pat. No. 7,549,934 which is a continuation-in-part of U.S. patent application Ser. No. 11/221,221 filed on Sep. 7, 2005, the disclosures of which are hereby incorporated herein by reference in their entirety.

BACKGROUND

The present invention relates to an improved golf club head. More particularly, the present invention relates to a golf club head with an improved striking face having the longest characteristic time shifted away from the geometric center of the hitting face.

The complexities of golf club design are well known. The specifications for each component of the club (i.e., the club head, shaft, grip, and subcomponents thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, center of gravity, inertia, material selection, and overall head weight. While this basic set of criteria is generally the focus of golf club engineering, several other design aspects are also often addressed. The interior design of the club head may be tailored to achieve particular characteristics, such as the inclusion of hosel or shaft attachment means, perimeter weights on the club head, and fillers within hollow club heads.

Golf club heads are also sufficiently strong to withstand the repeated impacts that occur during collisions between the golf club and the golf ball. The loading that occurs during this transient event can create a peak force of over 2,000 lbs. Thus, a major challenge is designing the club face and body to resist permanent deformation or failure by material yield or fracture. Conventional hollow metal wood drivers made from titanium typically have a uniform face thickness exceeding 2.5 mm to ensure structural integrity of the club head.

Players generally seek a metal wood driver and golf ball combination that delivers maximum distance and landing accuracy. The distance a ball travels after impact is dictated by the magnitude and direction of the ball's translational velocity and the ball's rotational velocity or spin. Environmental conditions, including atmospheric pressure, humidity, temperature, and wind speed further influence the ball's flight. However, these environmental effects are beyond the control of the golf equipment manufacturer. Golf ball landing accuracy is driven by a number of factors as well. Some of these factors are attributed to club head design, such as center of gravity and club face flexibility.

Generally, golf ball travel distance is a function of the total kinetic energy imparted to the ball during impact with the club head, neglecting environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball, as well as the club. Since the collision is not perfectly elastic, a portion of energy is dissipated in club head vibration and in viscoelastic relaxation of the ball. Viscoelastic relaxation is a material property of the polymeric materials used in most commercially-available golf balls.

Viscoelastic relaxation of the ball is a parasitic energy source, which is dependent upon the rate of deformation of the ball. To minimize this effect, the rate of deformation of the ball should be reduced. This may be accomplished by allowing more club face deformation during impact which increases the duration of contact between the ball and the club face. Since metallic deformation may be purely elastic, the strain energy stored in the club face is returned to the ball after impact thereby increasing the ball's outbound velocity after impact.

A variety of techniques may be utilized to vary the deformation of the club face, including uniform face thinning, thinned faces with ribbed stiffeners and varying thickness, among others. These designs should have sufficient structural integrity to withstand repeated impacts without permanently deforming the club face. In general, conventional club heads also exhibit wide variations in initial ball speed after impact, depending on the impact location on the face of the club.

The United States Golf Association (USGA), the governing body for the rules of golf in the United States, issues specifications for the performance of golf balls and clubs. One such USGA rule limits the duration of the contact between the golf ball and the geometrical center of a club face, called the "characteristic time", to less than 257 microseconds. To maximize golf ball travel distance, a golf club's spring-like effect should be maximized while remaining within these rules. Hence, there remains a need in the art for a club head that has maximized performance in terms of carry distance and club face deformation while adhering to USGA characteristic time rules at the geometric center of the hitting face.

SUMMARY OF THE INVENTION

A golf club head comprising a hitting face having a central zone and an intermediate zone. The central zone comprises a raised inner portion and a raised outer portion, wherein the raised inner portion is thicker than the raised outer portion. Both the inner and outer portions are thicker than the intermediate zone. On this hitting face, the location of longest characteristic time is offset from a geometric center of the hitting face.

One or both of the raised portions of the central zone can have the shape of a rhombus. Transition zones with varying thickness can connect the raised inner portion to the raised outer portion and the outer portion to the intermediate zone.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 2 is a front schematic view of a hitting face insert according to the present invention;

FIG. 3 is a cross-sectional view of the hitting face of FIG. 2 taken along line 3-3 thereof;

DETAILED DESCRIPTION

As illustrated in the accompanying drawings and discussed in detail below, the present invention is directed to a club head with a longest characteristic time shifted away from the geometric center of the club head. U.S. Pat. No. 6,605,007, which is incorporated herein in its entirety, discloses an improved golf club that also produces a relatively large "sweet zone" or zone of substantially uniform high initial velocity or high coefficient of restitution (COR). Increases or decreases in COR correspond generally but not directly to increases and decreases in the spring-like effect and characteristic time of a golf club head as many of the same design function affect both properties, such as material selection and club hitting face thickness.

Figure 1:
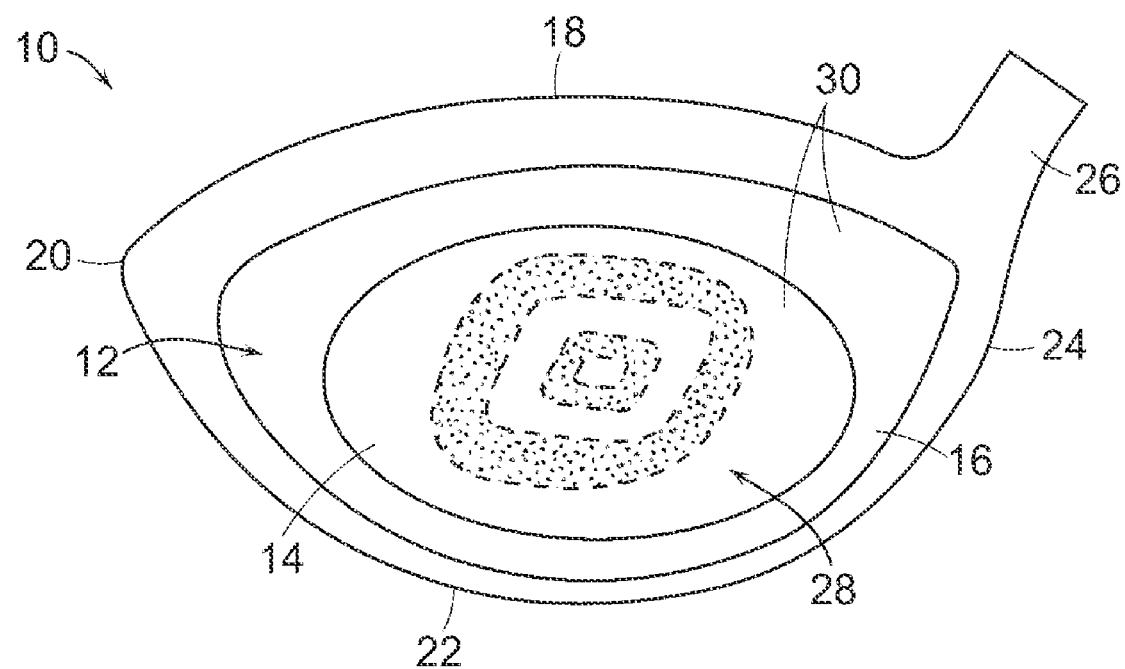
FIG. 1 is a front view of a driver golf club head (not drawn to scale) in accordance with the present invention.

Referring to FIG. 1, one embodiment of a configuration of a hitting face where the location of longest characteristic time is shifted away from the geometric center of hitting face 2 is shown. Hollow metal wood club head 10 has a hitting face 12 which includes a face insert 14 and face support 16. Face insert 14 fits into a similarly shaped opening in face support 16 and is affixed therewithin by any method known in the art, such as by welding. Club head 10 also has crown 18, toe 20, sole 22, heel 24 and hosel 26.

As shown in FIG. 2, disposed on the inner-cavity-facing surface of face insert 14 is central zone 28, which preferably has a generally elliptical shape. As defined here, the term "rhombus", "rhombi", "ellipse" or "elliptical" refers to non-circular shapes that have discernable major axis and minor axis, and include, but are not limited to, any quadrilateral shapes, geometrical ellipses, quadrilateral shapes with one or more rounded corner(s) and unsymmetrical elliptical shapes. The "major axis" is defined as the axis coinciding with the longest length that can be drawn through the non-circular shapes without intersecting the perimeter of the shapes at more than two locations, i.e., at the start and end points of said length. The "minor axis" is orthogonal to the major axis at or near its midpoint. As used herein, the term "concentric" refers to shapes that substantially encircle or surround other shapes.

Central zone 28 preferably includes a varying thickness profile, where the minor axis of central zone 28 is shorter than the major axis of central zone 28. Central zone 28 is preferably positioned within face insert 14 such that the major axis of central zone 28 is aligned in the direction of the low toe to high heel, so that a sweet spot can be established in the direction of high toe to low heel. This sweet spot advantageously coincides with the typical impact patterns created by golfers as discussed in detail in the parent '221 patent application. As central zone 28 is stiffer than the surrounding zones, the point of longest characteristic time is shifted away from a geometric center of hitting face 12, with the geometric center being preferably located within central zone 28. Central zone 28 is generally more rigid than the rest of hitting face 12 and in a preferred embodiment comprises an inner rhombus/ellipse and an outer rhombus/elliptical ring.

Central zone 28 is comparatively rigid and surrounding intermediate zone 30 is relatively flexible so that upon ball impact intermediate zone 30 includes the area of hitting face 12 less the area of central zone 28. Intermediate zone 30 of face 12 deforms upon impact with a golf ball, i.e., provides a desirable spring-like effect to provide high ball velocity, while central zone 28 is substantially undeformed so that the ball flies on-target. Thus, upon ball impact the deformation of intermediate zone 30 allows central zone 28 to move into and out of club head 10 substantially as a unit. Since central zone 28, which incorporates the geometric center, deforms less than intermediate zone 30, the characteristic time is relocated away from the geometrical center of hitting face 12.

The above effect can be accomplished by providing central zone 28 an aggregate first flexural stiffness and intermediate zone 30 with a second flexural stiffness. Flexural stiffness (FS) is defined as each portion's average elastic modulus (E) times each portion's average thickness (t) cubed or ($FS=Et^3$). The calculation of averages of modulus and thickness is fully disclosed in the parent application and in the '007 patent, which have already been incorporated by reference in their entireties. The determination of FS when the thickness varies such as in the present invention or when the material is anisotropic is also fully discussed in the parent patent application and in the '007 patent.

Since the flexural stiffness is a function of material and thickness, the following techniques can be used to achieve the substantial difference between the flexural stiffness of central zone 28 and intermediate zone 30: 1) different materials can be used for each portion, 2) different thicknesses can be used for each portion, or 3) a combination of different materials and thickness can be used for each portion. For example, in a preferred embodiment, the thickness of central zone 28 is greater than the thickness of intermediate zone 30 and the material for both portions is the same so that the FS of central zone 28 is greater than the FS of intermediate zone 30. Central zone 28 may have a uniform thickness, or the thickness may vary.

Preferably, the ratio of FS (28—aggregate) to FS (30) is at least 1.2, preferably at least 1.5, more preferably 2.0. The required flexural stiffness ratio may also be obtained through the use of structural ribs, reinforcing plates, thickness parameters or by the double-rhombus shape shown in FIG. 1. U.S. Pat. No. 7,029,403 and the '007 patent describe in detail a preferred range of ratios of flexural stiffness between central zone 28 and intermediate zone. The '403 patent is also incorporated herein by reference in its entirety.

The performance of hitting face 12 is optimized over the entire area of face 12 instead of at or around the geometric center of hitting face 12. As USGA club conformance standards using the pendulum test method described herein are based upon the characteristic time, i.e., the duration of contact between a probe and the club hitting face, only at the geometric center of the hitting face, hitting face 12 may have locations having longer characteristic times while staying within the USGA rules. This shifting of the location of longest characteristic time is found on hitting face structures that raise the stiffness of central zone 28 or, similarly, decreases the stiffness of intermediate zone 30. Several examples of such hitting face configurations are discussed below and further described or disclosed in the parent '221 application, as well as the '403 and '007 patents.

FIG. 2 shows in more detail face insert 14 of hitting face 12 shown in FIG. 1. Face insert 14 is configured to be inserted into any club head having an opening formed therein to receive face insert 14. In order to increase the FS of the center of face insert 14, inner central zone 14a and outer central zone 14b are provided on rear of face insert 14. Inner central zone 14a has a surface area which is less than the surface area of outer central zone 14b, with inner central zone 14a connected to outer central zone 14b by a first transition zone 17a. Preferably, the area occupied by inner central zone 14a is between about 10% and about 80% of the area occupied by the outline of outer central zone 14b. A second transition zone 17b connects outer central zone 14b with a portion of intermediate zone 30. As such, when inner central zone 14a is stacked onto outer central zone 14b which, in turn, is positioned on intermediate zone 30, inner central zone 14a and outer central zone 14b create a stepped profile as shown in FIG. 3, except for transition zones 17a and 17b.

Preferably, inner central zone 14a and outer central zone 14b have similar elliptical shapes, which in this embodiment are shown as rhombi having rounded corners. However, inner central zone 14a and outer central zone 14b may have the same or different configurations, which may be selected from any known geometric shape. As such, inner central zone 14a and outer central zone 14b form substantially flat surfaces connected by tapering first transition zone 17a. Therefore, the thickest portion of face insert 14 coincides with any point on inner central zone 14a. In another embodiment, inner central zone 14a may have another configuration, such as rounded, so that the thickest point of face insert 14 is a specific location on inner central zone 14a. As such, inner central zone 14a has a higher flexural stiffness than the surrounding areas, and, correspondingly, shorter characteristic time. As the point of highest characteristic time will be located on a point of hitting face 12 which has a lower flexural stiffness than inner central zone 14a, preferably, inner central zone 14a is positioned at or proximate to the geometric center of hitting face 12, so that the point of longest characteristic time is shifted away from the geometric center of hitting face 12.

Preferably, face insert 14 is made by forging, milling, or stamping and forming. In an exemplary process, a malleable metal suitable for use as a hitting face, such as titanium, titanium alloy, carbon steel, stainless steel, beryllium copper, and other formable metals, is heated and then hammered into the desired shape of the face insert. Examples of some appropriate metals include, but are not limited to, titanium 6-4 alloy, titanium 15-3-3-3 alloy, titanium 20-4-1 alloy, and DAT 55 and DAT 55G, titanium alloys available from Daido Steel of Tokyo, Japan. Preferably, face insert 14 is made as a unitary piece, with inner central zone 14a, outer central zone 14b, and a portion of intermediate zone 30 fashioned from a single plate of material, e.g. by forging. Alternatively, inner central zone 14a and outer central zone 14b may be made as separate pieces which are then affixed to a plate forming intermediate zone 30 using any method known in the art, such as welding, brazing, hot isotonic pressing, using an adhesive, mechanical fixtures, and the like. In such a case, inner central zone 14a and outer central zone 14b could be made from any material known in the art, such as metals, composites, and the like. For example, it may be desirable to manipulate the center of gravity of the club head by using multiple materials or composites. The benefits of having thickened inner central zone 14a and outer central zone 14b can be achieved by using a lightweight, relatively stiff material, such as a graphite composite, which sufficiently stiffens inner central zone 14a and outer central zone 14b but does not significantly increase the weight of hitting face 12.

The material properties of face insert 14 can also be affected by the method chosen to form face insert 14. For example, face insert 14 is preferably stamped or milled from sheet metal after the metal has been cold rolled or cold worked in order to align the crystal grains of the metal. Stamped metal made in this fashion produces a stronger hitting face than other manufacturing techniques. Further, face insert 14 is then positioned within hitting face 12 so that the grain flow pattern of face insert 14 runs in a sole-to-crown direction. Alternatively, the grain flow pattern of face insert 14 may run in a heel-to-toe direction or in a diagonal direction. Other methods known in the art may also be used to manufacture face insert 14, such as forging and casting.

Hitting face 12 in any of the embodiments described above is preferably cast, formed, milled, chemically milled, PM-sintered, or any combination thereof. The body of club 10 is preferably cast. The inner cavity of club head 10 may be empty, or alternatively may be filled with foam or other low specific gravity material. It is preferred that the inner cavity has a volume greater than 150 cubic centimeters, and more preferably greater than 350 cubic centimeters, and most preferably 450 cubic centimeters or more. Preferably, the mass of the inventive club head is greater than 150 grams but less than 230 grams. Further part and manufacturing details and additional test results regarding the COR values of inventive club heads are discussed in detail in the parent '221 application and the '403 and '007 patents.

Table 1 shows how the characteristic time varies between the hitting face of the inventive club and the hitting face of a club made according to an embodiment shown and described in the parent '221 application. The inventive club is a hollow metal wood club head having a hitting face made generally in accordance with the embodiment shown in FIGS. 2 and 3. Both the inner central zone 14a and outer central zone 14b are rounded-corner rhombi, with the inner central zone positioned substantially over the geometric center of the inventive club hitting face 12.

The exemplary club hitting face is approximately 4.4 mm (0.173 inch) in thickness in the inner central zone ($t_{14a}$), approximately 3.4 mm (0.134 inch) in thickness in the outer central zone ($t_{14b}$), and approximately 2.4 mm (0.094 inch) in thickness in the intermediate zone ($t_{30}$). The inner central zone rhombus sides are each about 2.54 mm long, and the outer central zone rhombus sides are each about 7.94 mm. The flexural stiffness or FS of inner central zone 14a is about 85,432; the FS of outer central zone 14b is about 39,701; and the FS of intermediate zone 30 is about 13,704. The flexural ratios are as follows:

FS(14a)/FS(14b)=2.15

FS(14b)/FS(30)=2.90

FS(14a)/FS(30)=6.23

Preferably, the FS ratio between the inner central zone to the outer central zone is at least about 1.2, preferably about 1.5 and more preferably at least about 2.0. The FS ratio between the outer central zone to the intermediate zone is at least about 1.2, preferably about 1.5 and more preferably at least about 2.0. The ratio between the inner zone and the intermediate zone is at least about 2.5, more preferably about 3.0 and more preferably about 3.5.

Figure 4:
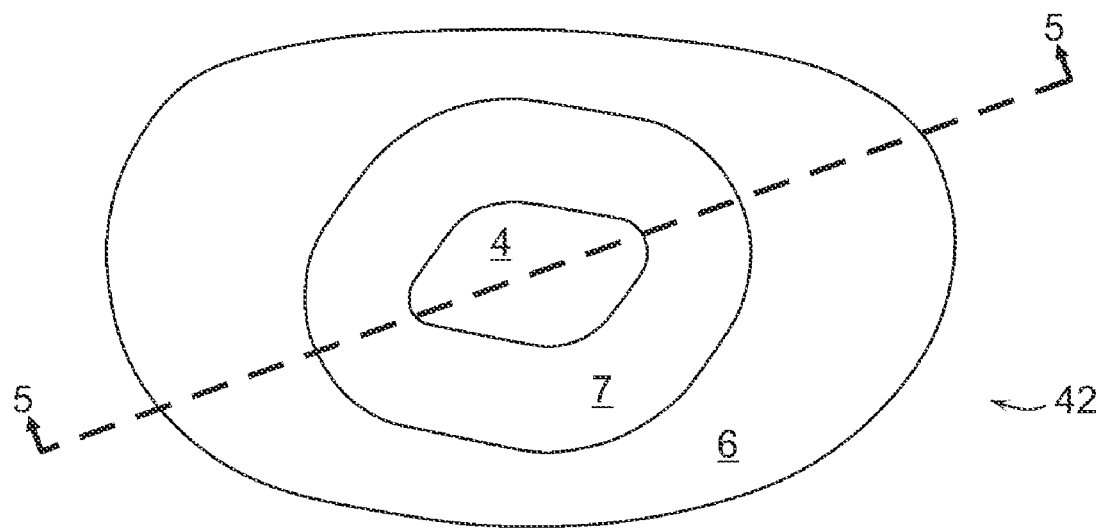
FIG. 4 is a schematic view of a club head showing zones of varying flexural thickness as disclosed in the parent '221 application and corresponds to FIG. 5 thereof.
Figure 5:
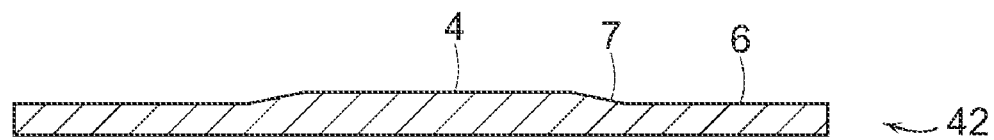
FIG. 5 is a cross-sectional view of the club head of FIG. 4 taken along line 5-5 thereof and corresponds to FIG. 5A of the parent '221 application.

A comparison club is made substantially according to FIG. 4, which corresponds to FIG. 5 from the parent '221 application. The comparison club has a hitting face 42 with a central zone 4 in the shape of a rounded-corner rhombus surrounded by a thinner intermediate zone 6 with a transitional zone 7 having a tapered thickness to join central zone 4 and intermediate zone 6 in a smooth radius. This smooth transition of thicknesses is shown more clearly in FIG. 5, which shows a cross-sectional view of hitting face. Each leg of the rounded-corner rhombus is about 6.35 mm.

Both the inventive club and the comparison club were tested using the USGA pendulum test, where the club head is inserted into a testing apparatus and hit with a weighted pendulum at the geometric center at several different speeds. The length of contact duration between the weighted pendulum and the club head hitting face is measured to determine the characteristic time of the club. In addition to the standard testing at the geometric center, however, the inventive club and the comparison club were tested at several off-center locations to determine characteristic times away from the geometric center of hitting face 42. As such, the overall flexibility of the hitting faces of the inventive club and the comparison club can be determined.

King Cobra M/SPEED 9.0° drivers with stock cast 6-4 Titanium head models were used in the test. One driver has the inventive face insert of FIGS. 2 and 3 and the other drive has the comparison insert of FIGS. 4 and 5 were. Both inserts were cast with 6-4 Titanium and chemically milled. The thickness in the central zone (4) of the comparison insert is about 4.3 mm (0.169 inch) and the thickness of the intermediate zone (6) of the comparison insert is about 2.8 mm (0.110 inch).

TABLE 1

Characteristic Times for Inventive Club, Comparison Club

| Testing Location on Hitting Face | Inventive Club Characteristic Time (μs) | Comparison Club Characteristic Time (μs) | Change in Characteristic Time (μs) |
|---|---|---|---|
| Geometric Center (GC) | 253 | 250 | +3 |
| Horizontally Offset Toward Heel from GC | 266 | 266 | — |
| Horizontally Offset Toward Toe from GC | 250 | 243 | +7 |
| Vertically Above GC, Directly | 250 | 235 | +15 |
| Vertically Below GC, Directly | 252 | 249 | +3 |
| Vertically Above GC, Offset Toward Toe | 256 | 248 | +8 |
| Vertically Below GC, Offset Toward Toe | 243 | 231 | +12 |
| Vertically Above GC, Offset Toward Heel | 271 | 269 | +2 |
| Vertically Below GC, Offset Toward Heel | 262 | 263 | −1 |

As can be seen in Table 1, in both clubs the characteristic time at the geometric center of the hitting face meets the USGA rule of less than 258 microseconds (μs). However, the inventive club is closer to the USGA limit, which means that the inventive club is more flexible at the geometric center than the comparison club. The highest characteristic times were measured toward the heel. Additionally, the characteristic time at nearly every tested location is higher for the inventive club than for the comparison club or substantially the same for both clubs. In other words, the inventive club face is able to flex more than the comparison club. As such, the spring-like effect of the inventive club is enhanced as compared to the comparison club, which should yield greater carry distances, even though both clubs satisfy USGA hitting face flexibility rules.

While various descriptions of the present invention are described above, it should be understood that the various features of each embodiment could be used alone or in any combination thereof. Therefore, this invention is not to be limited to only the specifically preferred embodiments depicted herein. Further, it should be understood that variations and modifications within the spirit and scope of the invention might occur to those skilled in the art to which the invention pertains. For example, any hitting face structure that increases stiffness at the geometric center as compared to the hitting face perimeter is appropriate, so the present invention is not limited to only those structures disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims. All publications discussed herein, including but not limited to patents, patent applications, articles, and books, are incorporated by reference in their entireties.

The invention claimed is:

1. A golf club head comprising:
    a hitting face comprising,
        a central zone comprising a raised inner portion having a first thickness, and a raised outer portion concentric with the inner portion and having a second thickness, wherein the first thickness is greater than the second thickness; and
        an intermediate zone concentric with the central zone and having a third thickness, wherein the second thickness is greater than the third thickness, and
    wherein a location of longest characteristic time is offset from a geometric center of the hitting face, and
    wherein the central zone is positioned at the geometric center of the hitting face and haves a major axis that aligns substantially in the direction of high heel to low toe.

2. The golf club head of claim 1, wherein the inner portion has a non-circular shape.

3. The golf club head of claim 1, wherein the outer portion has a non-circular shape.

4. The golf club head of claim 1, wherein the inner portion is in the shape of a rhombus.

5. The golf club head of claim 1, wherein the outer portion is in the shape of a rhombus.

6. The golf club head of claim 1, wherein the inner portion defines a first surface area and the outer portion defines a second area, and wherein the first area is between about 10% and 80% of the second area.

7. The golf club head of claim 1, wherein the location of longest characteristic time is offset from the geometric center toward the club head's toe.

8. The golf club head of claim 1, wherein the location of longest characteristic time is offset from the geometric center toward the club head's crown.

9. The golf club head of claim 1, wherein the location of longest characteristic time is offset from the geometric center toward the club head's heel.

10. The golf club head of claim 1, wherein a first transition zone with varying thickness connects the raised inner portion to the raised outer portion.

11. The golf club head of claim 1, wherein a second transition zone with varying thickness connects the raised outer portion to the intermediate zone.

12. The golf club head of claim 1, wherein the ratio between the flexural stiffness of the central zone to flexural stiffness of the intermediate zone is at least about 1.2.

13. The golf club head of claim 12, wherein the ratio between the flexural stiffness of the central zone to flexural stiffness of the intermediate zone is at least about 1.5.

14. The golf club head of claim 13, wherein the ratio between the flexural stiffness of the central zone to flexural stiffness of the intermediate zone is at least about 2.0.

15. The golf club head of claim 1, wherein the ratio between the flexural stiffness of the raised inner portion to flexural stiffness of the raised outer portion is at least about 1.2.

16. The golf club head of claim 15, wherein the ratio between the flexural stiffness of the raised inner portion to flexural stiffness of the raised outer portion is at least about 1.5.

17. The golf club head of claim 16, wherein the ratio between the flexural stiffness of the raised inner portion to flexural stiffness of the raised outer portion is at least about 2.0.

18. The golf club head of claim 1, wherein the ratio between the flexural stiffness of the raised inner portion to flexural stiffness of the intermediate zone is at least about 2.5.

19. The golf club head of claim 18, wherein the ratio between the flexural stiffness of the raised inner portion to flexural stiffness of the intermediate zone is at least about 3.0.

20. The golf club head of claim 19, wherein the ratio between the flexural stiffness of the raised inner portion to flexural stiffness of the intermediate zone is at least about 3.5.

21. The golf club head of claim 1, wherein the ratio between the flexural stiffness of the raised outer portion to flexural stiffness of the intermediate zone is at least about 1.2.

22. The golf club head of claim 21, wherein the ratio between the flexural stiffness of the raised outer portion to flexural stiffness of the intermediate zone is at least about 1.5.

23. The golf club head of claim 22, wherein the ratio between the flexural stiffness of the raised outer portion to flexural stiffness of the intermediate zone is at least about 2.0.

* * * * *